United States Patent [19]

Repperger et al.

[11] Patent Number: 5,337,743

[45] Date of Patent: Aug. 16, 1994

[54] FATIGUE INDICATOR BASED ON ARTERIAL OXYGEN

[75] Inventors: Daniel W. Repperger; Lloyd D. Tripp, both of Dayton, Ohio

[73] Assignee: The United States of America as represented by the Secretary of the Air Force, Wright-Patterson Air Force Base, Ohio

[21] Appl. No.: 77,799

[22] Filed: Jun. 17, 1993

[51] Int. Cl.$^5$ ............................................. A61B 5/00
[52] U.S. Cl. ................................. 128/633; 128/632; 128/666; 356/41; 364/413.03
[58] Field of Search .................... 128/632–634, 128/666; 356/41; 600/19, 20

[56] References Cited

U.S. PATENT DOCUMENTS

| | | | |
|---|---|---|---|
| H1,039 | 4/1992 | Tripp et al. | 128/206.28 |
| 3,587,438 | 6/1971 | Foster | 98/1.5 |
| 4,057,205 | 11/1977 | Vensel | 244/118 |
| 4,164,898 | 8/1979 | Burgess et al. | 98/1.5 |
| 4,224,861 | 9/1980 | Sands | 98/1.5 |
| 4,553,474 | 11/1985 | Wong et al. | 98/1.5 |
| 4,736,731 | 4/1988 | Van Patten | 128/1 A |
| 4,832,035 | 5/1989 | Cho et al. | 128/633 |
| 4,922,919 | 5/1990 | Novack | 128/633 |

OTHER PUBLICATIONS

Tripp, Jr., Ear Canal Pulse/Oxygen Staturation Measuring Device 07/767,962 Ag Inv 18609.

Primary Examiner—Lee S. Cohen
Assistant Examiner—Robert L. Nasser
Attorney, Agent, or Firm—Fredric L. Sinder; Thomas L. Kundert

[57] ABSTRACT

A new warning system for informing an aircrew member undergoing high acceleration, or other brain oxygen-depleting environmental stressors, of the time remaining before fatigue sets in and the aircrew member will no longer be able to maintain straining maneuvers fighting the effects of high acceleration utilizes the new discovery that pilots and other aircrew members experience performance-ending fatigue at about the same percentage level of blood oxygen saturation. The particular percentage varies individually, but is nearly always the same for a single individual. The warning system uses a non-invasive monitor to measure blood oxygen saturation at different times and to compute from those measurements the amount of time remaining before the individual percentage blood oxygen saturation at which fatigue or exhaustion will occur for that individual will be reached. That remaining time is displayed to the aircrew member on an instrument panel display. The warning system can also be used to display to an aircrew member the time remaining before a preselected level of decreased cognitive function is reached.

9 Claims, 4 Drawing Sheets

FATIGUE INDICATOR BASED ON ARTERIAL OXYGEN

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems for protecting aircrew members from the adverse physiological effects of brain oxygen-depleting environmental stressors, and more particularly to a warning system for informing an aircrew member undergoing high acceleration of the time remaining before fatigue sets in and the aircrew member will no longer be able to maintain straining maneuvers intended to fight the effects of high acceleration.

Many types of environmental stressors deplete the oxygen available to an aircrew member. For example, while flying simulated or actual combat maneuvers, a fighter pilot's body undergoes very high accelerations from the rapid changes in speed and direction. These accelerations are generally expressed in units of g, the acceleration of a mass at the surface of the Earth due to gravity. The accelerations of greatest concern to a pilot are those that occur along the vertical Z-axis of the cockpit when the pilot pulls back hard on the aircraft control stick to accomplish a rapid climb or a fast banked turn. The pilot's oxygen-carrying blood is forced away from its regular path between the heart-lungs and the brain and pools toward the blood vessels of the lower extremities. At sufficiently high G's, or after a sufficient length of time at high G's, the pilot's field of vision narrows as blood flow to the retinas is reduced, and the pilot will finally lose consciousness due to insufficient blood flow to the brain.

High altitude is another environmental stressor that depletes the oxygen available to an aircrew member. Whether the decreased oxygen level is from hypoxic hypoxia (decreased blood oxygen levels from decreased available oxygen in the atmosphere) or from stagnant hypoxia (blood pooling in the lungs and other body regions during exposure to hypergravity), the physiological end result is the same.

Aircrew members fight the adverse effects of high G's by straining maneuvers, isometrically tensing the muscles of their torso and extremities to squeeze shut the blood vessels and force blood flow to continue in the upper part of the body. These straining maneuvers typically can be maintained for only a limited period of time before fatigue sets in and the aircrew member can no longer resist the effects of high G's. Without warning of the onset of fatigue, the aircrew member may experience G-induced loss of consciousness (GLOC) before being able to take steps to reduce the environmental stressor, such as by moving the control stick to unload the aircraft.

Aircrew members fight the adverse effects of other brain oxygen-depleting environmental stressors by a variety of other methods, such as by different breathing procedures or by breathing supplemental oxygen during high altitude flight. A pilot may also descend the aircraft to a flight level below 10,000 ft.

The prior art includes various non-invasive loss of consciousness monitoring devices for aircrew members. Two useful examples of such devices, both of which have a co-inventor of this invention as an inventor or co-inventor, are "Ear Canal Pulse/Oxygen Saturation Measuring Device," U.S. Pat. No. 5,213,099; and, "Intrusion-Free Physiological Condition Monitoring of Flyers," Statutory Invention Registration (SIR) No. H1039, both of which are incorporated by reference into this description. Those two monitoring devices non-invasively monitor blood oxygen saturation levels so that when monitored blood oxygen saturation levels fall to a level indicating imminent unconsciousness, an alarm can be sounded or control of the aircraft removed from the pilot and the aircraft unloaded to reduce G-loading.

The prior art has not, however, explored the possibility of displaying blood oxygen saturation levels to the pilot or other aircrew member so that they can respond to that information before GLOC occurs. Part of the reason for this is that, except for actual GLOC, or other caused unconsciousness, the practical physiological meaning of various levels of blood oxygen saturation has not been well understood. Without such information, the ability to monitor in realtime blood oxygen saturation levels has been of limited utility.

Thus it is seen that there is a need for discovery of the practical physiological effects of different blood oxygen saturation levels.

It is also seen that there is a need for apparatus and methods for utilizing such discovered information that will help aircrew members avoid the harmful effects of brain oxygen-depleting environmental stressors.

It is, therefore, a principal object of the present invention to provide an apparatus and method for measuring blood oxygen saturation levels of an aircrew member and, using that information, displaying to the aircrew member useful information concerning the adverse effects of high $G_z$ acceleration and brain oxygen depletion.

It is a feature of the present invention that it incorporates a discovery that relates percentage blood oxygen saturation to the time remaining before an aircrew member will no longer be able to maintain performance.

It is another feature of the present invention that it displays to an aircrew member the time remaining before that aircrew member will no longer be able to maintain performance.

It is an advantage of the present invention that it enables aircrew members to make knowledgeable decisions during combat or other high intensity activities about, for example, the time of initiation and the duration of combat maneuvers.

It is another advantage of the present invention that because aircrew members will have a realtime display of the time remaining before performance-ending fatigue sets in, they can, and will, develop techniques to extend that time and increase overall performance.

It is an outstanding advantage of the present invention that it is an incentive to better performance. Because a pilot can now be shown the time remaining during which he or she can expect to continue a high level of performance, despite the presence of environmental stressors, he or she will try harder to reach and maintain that level of performance for at least the period of time displayed and, more likely in view of the competitive nature of pilots, even to exceed it.

These and other objects, features and advantages of the present invention will become apparent as the description of certain representative embodiments proceeds.

SUMMARY OF THE INVENTION

The present invention provides a new pilot indicator that warns a pilot undergoing brain oxygen-depleting environmental stressors of the time remaining before fatigue will set in and the pilot will no longer be able to continue performance. The unique discovery of the present invention is that pilots, or any person undergoing oxygen-depleting environmental stressors, experiences performance-ending fatigue at about the same percentage level of blood oxygen saturation. The particular percentage varies with individuals, but is nearly always the same for that individual. By extrapolating from realtime measurements of blood oxygen saturation the slope of a line describing a pilot's changing blood oxygen saturation percentages, the time remaining before fatigue will set in for that individual pilot can be calculated and displayed to the pilot so that he or she can take steps to reduce the environmental stressor or increase blood oxygen before fatigue sets in.

Accordingly, the present invention is directed to an indicator system for showing a person undergoing brain oxygen-depleting environmental stressors the time remaining before a performance-limiting event occurs, comprising means for measuring percentage blood oxygen saturation levels, computer means for extrapolating from successive measurements of percentage blood oxygen saturation levels the time remaining before a preselected level of percentage blood oxygen saturation is reached, and means for displaying to the person the computed time remaining before the preselected level of percentage blood oxygen saturation is reached. The display means may be legended as displaying the time remaining before performance-ending fatigue occurs. The display means may also be legended as displaying the time remaining before a preselected level of decreased cognitive function is reached. The preselected level of percentage blood oxygen saturation may be predetermined by testing of the person undergoing the environmental stressors. The person may be an aircraft pilot. The means for measuring percentage blood oxygen saturation levels may be positioned so that it measures arterial blood oxygen saturation levels near the brain. The environmental stressor may be high g forces from rapid changes in speed and acceleration. The environmental stressor may also be high altitude. The measuring means may be non-invasive.

The present invention is also directed to a method for showing a person undergoing brain oxygen-depleting environmental stressors the time remaining before a performance-limiting event occurs, comprising the steps of measuring the person's percentage blood oxygen saturation levels, extrapolating from successive measurements of percentage blood oxygen saturation levels the time remaining before a preselected level of percentage blood oxygen saturation is reached, and displaying to the person the extrapolated time remaining before the preselected level of percentage blood oxygen saturation is reached. The method may further comprise the step of displaying to the person a legend stating that the time displayed is the time remaining before performance-ending fatigue occurs. The method may also further comprise the step of displaying to the person a legend stating that the time displayed is the time remaining before a preselected level of decreased cognitive function is reached.

DESCRIPTION OF THE DRAWINGS

The present invention will be more clearly understood from a reading of the following detailed description in conjunction with the accompanying drawings wherein.

DETAILED DESCRIPTION

Figure 1:
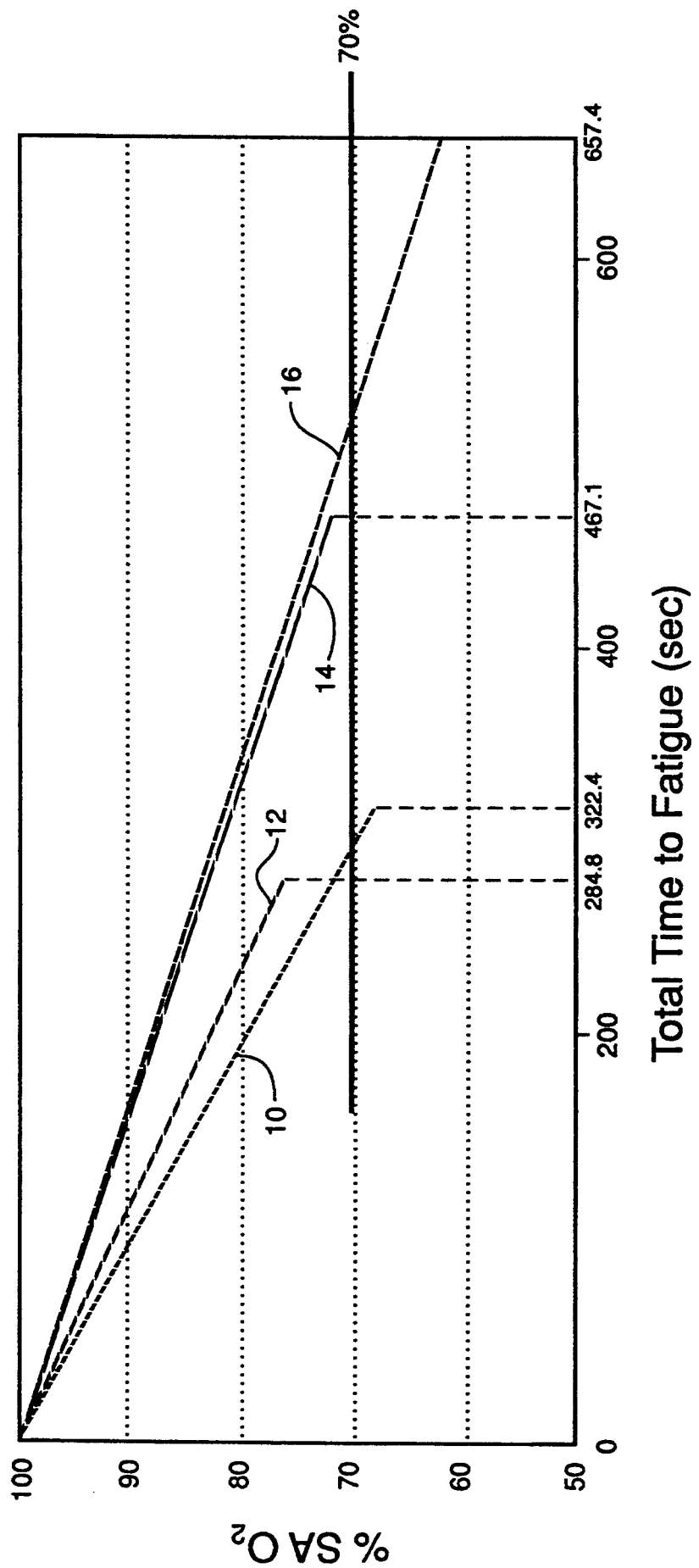
FIG. 1 is a graph of total time to fatigue versus percentage blood oxygen saturation for centrifuge test subjects wearing different types of anti-G suits.

Referring now to FIG. 1 of the drawings, there is shown a graph of total time to fatigue versus percentage blood oxygen saturation for centrifuge test subjects wearing different types of anti-G suits. Percentage blood oxygen is labeled % $SAO_2$ along the vertical axis and Total Time to Fatigue (also referred to as Total Time to Exhaustion) is shown in seconds along the horizontal axis. Fatigue, or exhaustion, is the point at which the test subject could no longer maintain sufficient resistance, typically through a variety of physical straining maneuvers, against the harmful effects of G forces so that the test subject could continue performance. Performance could be piloting an aircraft or comparable tasks used in centrifuge tests. Trace 10 shows the averaged total time to exhaustion for test subjects wearing a standard anti-G suit. Trace 12 shows the average total time to exhaustion for test subjects wearing a retrograde inflation anti-G suit (RIAGS) with arm cuffs (RIAGS With C). Trace 14 shows the average total time to exhaustion for test subjects wearing a RIAGS alone. And, Trace 16 shows the average total time to exhaustion for test subjects wearing a RIAGS with capstan sleeves (RIAGS with S1).

FIG. 1 shows that, on average, test subjects fatigued or voluntarily terminated the centrifuge test run at about 70% $SAO_2$, independent of the type of anti-G suit or other conditions. The type of anti-G suit only changed the slope of the % SA $O_2$ curve. While there is some variation among individuals at what % $SAO_2$ they fatigue, the % $SAO_2$ at which each individual fatigues does not vary for that individual regardless of type of anti-G suit or other conditions.

Figure 2:
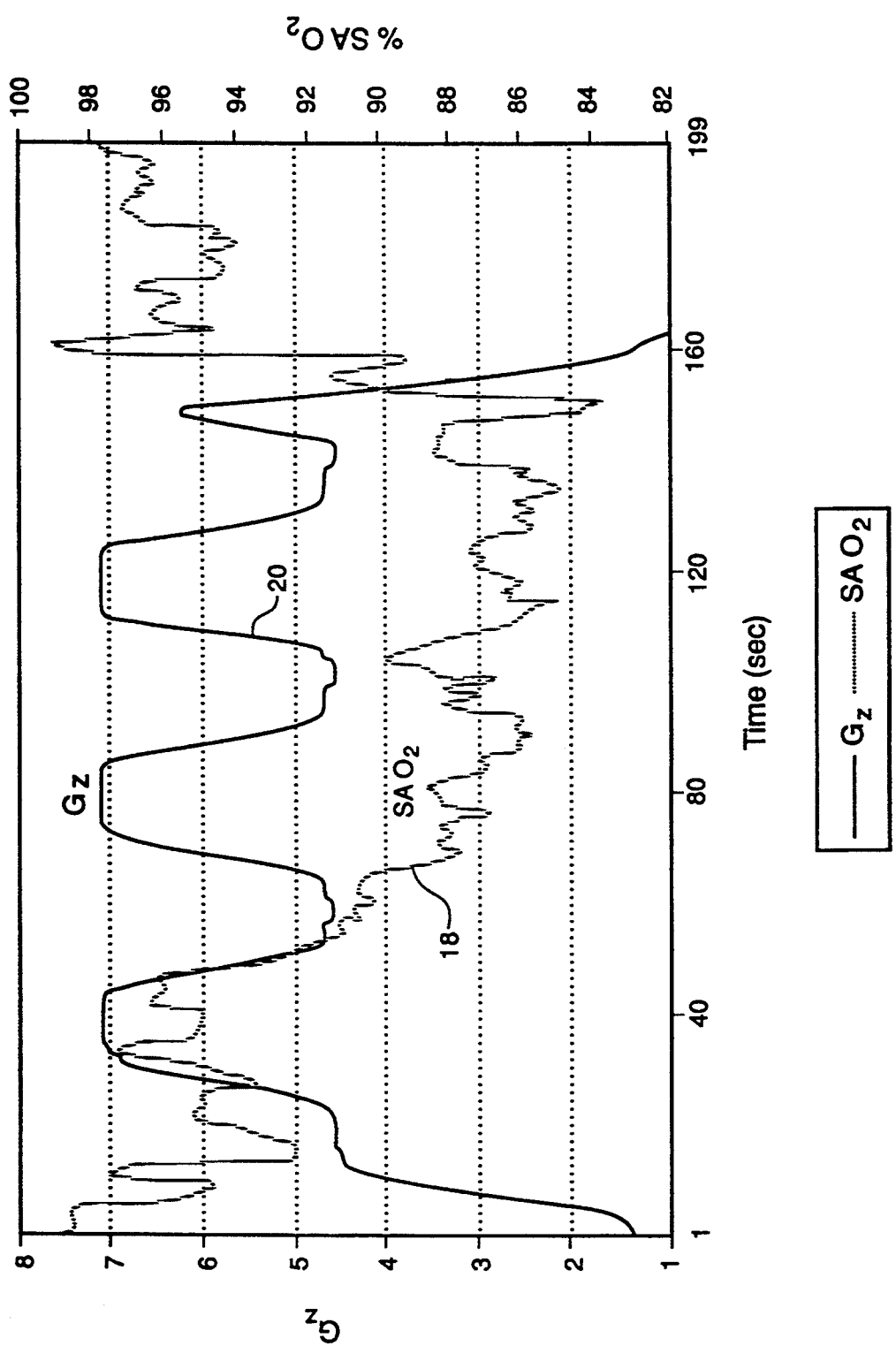
FIG. 2 is an example graph of both $G_z$ and percentage blood oxygen saturation over time for an individual centrifuge test subject.

FIG. 2 shows a graph of both $G_z$ and percentage blood oxygen saturation over time for an individual test subject undergoing a typical centrifuge test run. $G_z$ is shown along the left vertical axis in units of g. % $SAO_2$ is shown along the right vertical axis. Duration is shown in seconds along the horizontal axis. Trace 18 shows % $SAO_2$ of the test subject over time and trace 20 shows the level of $G_z$ at each point in time. At time equals one second, the baseline % $SAO_2$ for the test subject is approximately 100%. As the test subject undergoes the fatigue process, % $SAO_2$ decreases until about 150 seconds when fatigue occurred and the test subject voluntarily terminated the run. Fatigue occurred for this test subject at about 85% $SAO_2$. When averaged among 7 test subjects, the average % $SAO_2$ at which the test subjects terminated the test run was about 70%, but, as stated earlier, it is very specific to an individual.

Figures 3, 4:
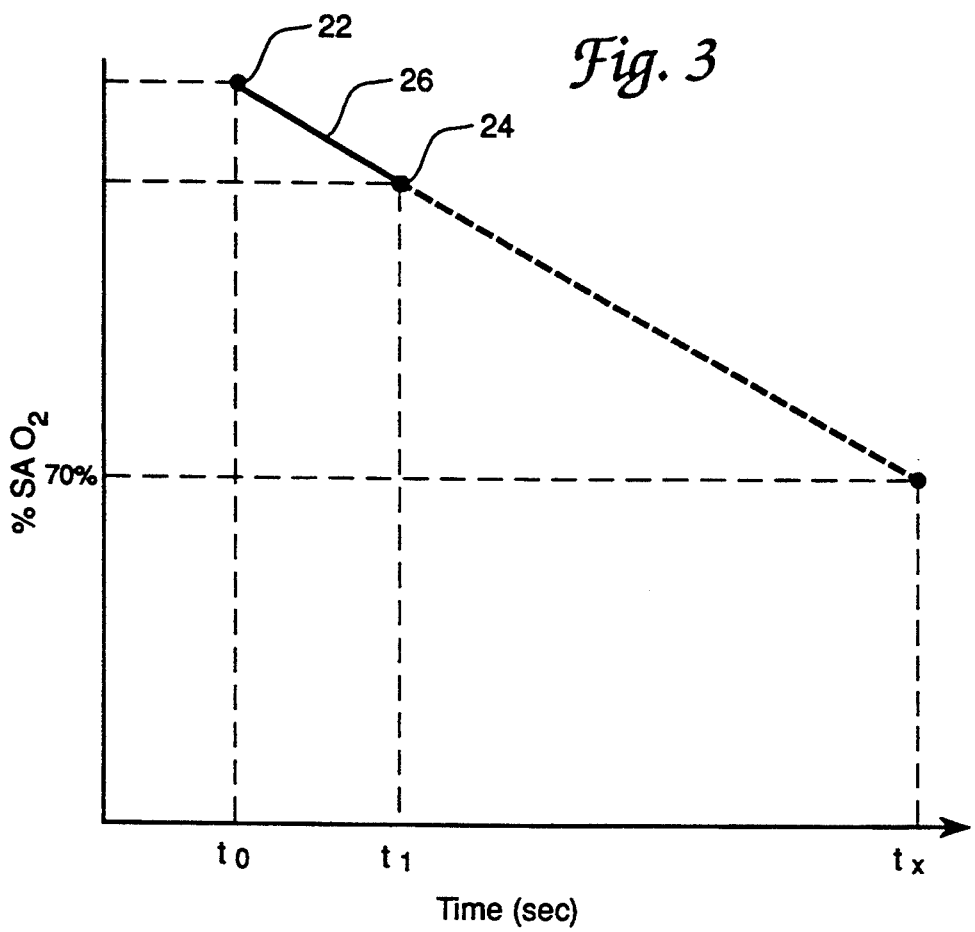
FIG. 3 is a graphical representation of operation of the present invention showing extrapolation to a future time when performance-ending fatigue will occur.
FIG. 4 is an example aircraft computer display according to the present invention for displaying to an aircrew member the time remaining before performance-ending fatigue will occur; and, FIG. 5 is a schematic view of a pilot indicator system according to the teachings of the present invention.

Inspection of the FIG. 1 graph shows that the relationship between time to fatigue and % $SAO_2$ is mostly linear. This means that the time to fatigue can be calculated from the slope of a graphical line plotting % $SAO_2$ against time and from the known % $SAO_2$ setpoint at which fatigue will set in. FIG. 3 shows a graphical representation of this calculation. Measurements 22 and 24 of blood oxygen saturation, preferably using a non-invasive blood oxygen saturation measuring device mounted on or near the head, are made at times $t_0$ and $t_1$ and a line 26 drawn between them. Line 26 is extended, or extrapolated, to the time $t_x$ where it crosses the % $SAO_2$ setpoint at which that individual has been shown, by testing, to experience fatigue.

In practice, this graphical representation of FIG. 3 will be calculated using a computer. FIG. 4 shows an example aircraft computer monitor display 28 displaying to an aircrew member the time remaining before performance-ending fatigue occurs. FIG. 4 shows the display as black on white although an actual aircraft monitor display would more likely be white on black or other background color. FIG. 4 is actually a display used during development of the present invention, but its use, with little modification, in an aircraft cockpit is obvious. The most important element of display 28 is the Time to Fatigue indication 30. A pilot or other aircrew member can quickly ascertain from indication, or display element, 30 the time remaining during which the pilot must finish the action then being taken which is causing the environmental stressor, or face possible catastrophic results.

FIG. 4 also displays the example calculation of Time to Fatigue indication 30 for a test subject previously tested to have personal setpoint of 67% at which fatigue would occur. In this case, four values of % $SAO_2$ were measured (99.3, 98.6, 96.7 and 95.9). The negative slopes were then calculated between adjacent points (negative slopes=0.7, 0.9 and 0.8) and the average slope then determined (average slope=0.8). Based on the last % $SAO_2$ measurement (95.9) and the calculated average slope of 0.8, the equation:

$$95.9 - 0.8 X \text{ (time to fatigue)} = 67\%$$

was solved for time to fatigue. This yields a time to fatigue=36.2 seconds which is displayed on the monitor.

Figure 5:
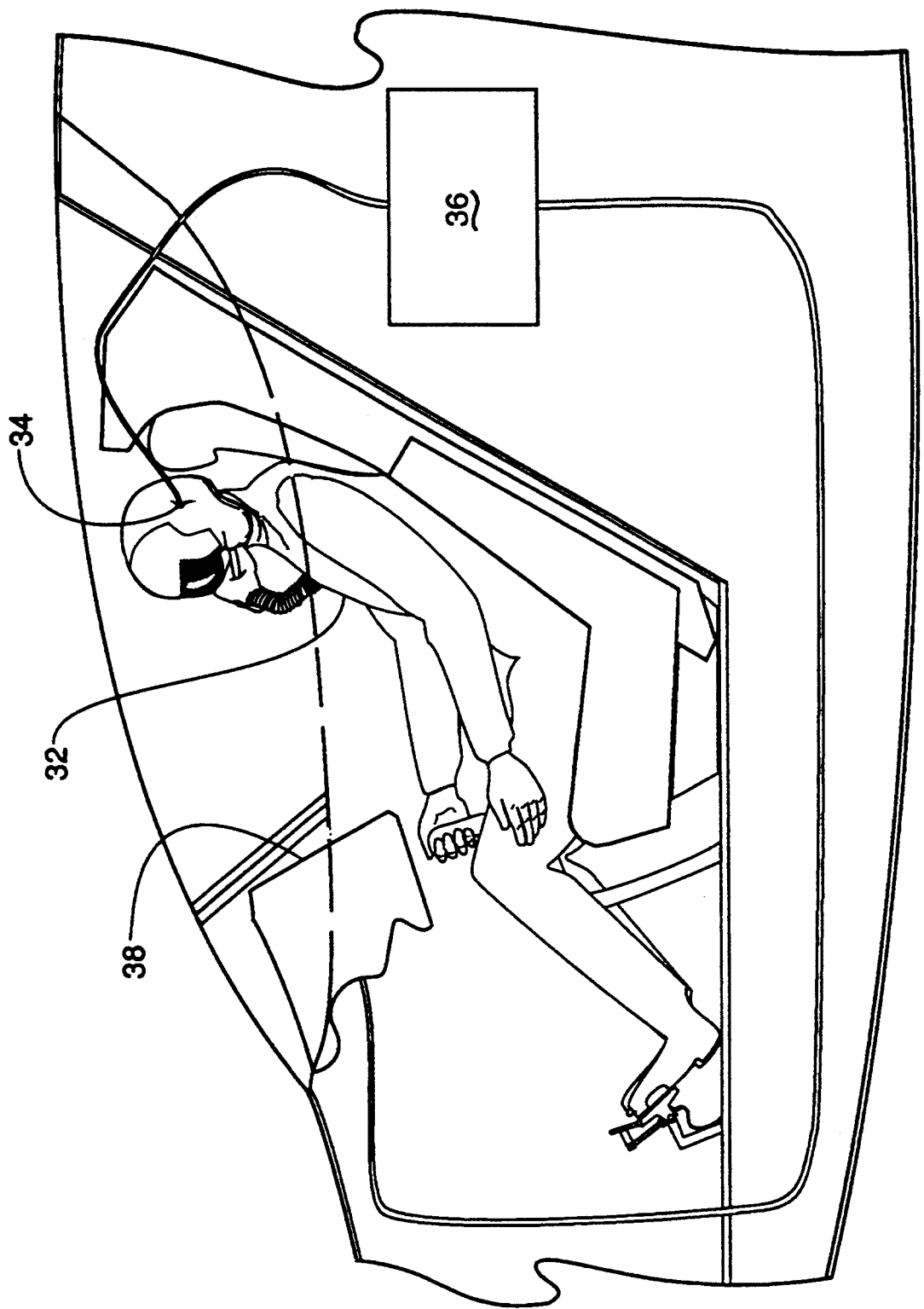

FIG. 5 shows a schematic view of a pilot indicator system built according to the teachings of the present invention. A pilot 32 has a non-invasive blood oxygen saturation monitor 34 attached near or on his head. Signals from blood oxygen saturation monitor 34 travel to computer 36 where they are sampled at regular time intervals and the slope of a line connecting the most recently sampled percentage blood oxygen saturation levels mathematically determined. From that slope, the time remaining before a preselected level of percentage blood oxygen saturation is reached is mathematically computed and sent to an instrument panel display 38 in front of pilot 32. The individual percentage blood oxygen saturation at which fatigue occurs is punched into the computer by the pilot, or a groundcrew member, before beginning a flight.

Those with skill in the art will readily see that a realtime display of time remaining before fatigue will enable pilots to develop methods for extending the time before fatigue occurs. By, for example, partially unloading the aircraft, instead of completely, the pilot can observe his or her computed time before exhaustion or fatigue increasing and gain more time to complete an action, which action may be impossible to complete in time if the pilot attempted to complete the action while maintaining a higher aircraft loading- The pilot now has an opportunity to balance, or trade-off, current levels of performance versus duration. Without the realtime feedback provided by the present invention, pilots have to guess how long they can maintain a desired level of performance. Pilots can now only roughly guess how long they have until GLOC by the extent to which their field of vision narrows.

Those with skill in the art will also readily see that the present invention may be extended to display useful information concerning prior art discoveries of the effects of reduced blood oxygen saturation levels. The prior art teaches that mental performance decreases significantly as a function of decreased oxygen levels. At some reduced level of percentage blood oxygen saturation, a pilot's level of cognitive function reduces below the point where the pilot can reasonably rely on his or her mental ability for quick decision making. This level will likely be higher than the level at which the pilot can still maintain an already begun and highly practiced flight maneuver. By predetermining for an individual pilot at what level of percentage blood oxygen that occurs, a substitute, or additional, legend could be added to the FIG. 4 display showing "Time to Decreased Cognitive Function=" or "Time to End of Useful Consciousness". As with the legend "Time To Fatigue=", these displays will permit a pilot to pace him or herself, thereby increasing overall performance.

The disclosed new system for warning aircrew members of impending performance-ending fatigue successfully demonstrates the use of discovering the practical physiological effects of different blood oxygen saturation levels and adapting those discoveries to an indicator system for displaying useful information that will help aircrew members avoid the harmful effects of brain oxygen-depleting environmental stressors. Although the disclosed apparatus is specialized, its teachings will find application in other areas where harmful physiological effects currently limit human performance and where feedback information, if discovered, would allow humans to overcome, in whole or in part, the present limits on their performance.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

I claim:

1. An indicator system for showing a person undergoing brain oxygen-depleting environmental stressors the time remaining before a performance-limiting event occurs, comprising:
   (a) means for repeatedly measuring percentage blood oxygen saturation levels:
   (b) computer means for repeatedly extrapolating from successive measurements of said percentage blood oxygen saturation levels the time remaining before a preselected level of percentage blood oxygen saturation is reached; and, (c) means for displaying to the person the computed time remaining before the preselected level of percentage blood oxygen saturation is reached, wherein the displaying means is an aircraft instrument panel display including a label stating that the time displayed is the time remaining before performance-ending fatigue occurs.

2. The indicator system according to claim 1, wherein the label on the aircraft instrument panel display states that the time displayed is the time remaining before a preselected level of decreased cognitive function is reached.

3. The indicator system according to claim 1, wherein the means for repeatedly measuring percentage blood oxygen saturation levels is positioned so that it measures arterial blood oxygen saturation levels near the brain.

4. A method for protecting an aircrew member from the adverse physiological effects of a brain oxygen-depleting environmental stressor, comprising the steps of:

(a) repeatedly measuring the aircrew member's percentage blood oxygen saturation level;

(b) repeatedly extrapolating from successive measurements of said percentage blood oxygen saturation levels the time remaining before a preselected level of percentage blood oxygen saturation is reached; and, (c) reducing the level of the brain oxygen-depleting environmental stressor before the preselected level of percentage blood oxygen saturation is reached.

5. The method for protecting an aircrew member from the adverse physiological effects of a brain oxygen-depleting environmental stressor according to claim 4, wherein the brain oxygen-depleting environmental stressor is high g forces from rapid changes in speed and acceleration of an aircraft and the step of reducing the level of the brain oxygen-depleting environmental stressor is unloading the aircraft.

6. The method for protecting an aircrew member from the adverse physiological effects of a brain oxygen-depleting environmental stressor according to claim 4, wherein the brain oxygen-depleting environmental stressor is high altitude of an aircraft and the step of reducing the level of the brain oxygen-depleting environmental stressor is reducing the altitude of the aircraft.

7. A method for extending the time an aircrew member undergoing a brain oxygen-depleting environmental stressor can perform before performance-ending fatigue occurs, comprising the steps of:

(a) repeatedly measuring the aircrew member's percentage blood oxygen saturation levels;

(b) repeatedly extrapolating from successive measurements of said percentage blood oxygen saturation levels the time remaining before a preselected level of percentage blood oxygen saturation is reached; and, (c) reducing the level of the brain oxygen-depleting environmental stressor until the extrapolated time remaining increases.

8. The method for extending the time an aircrew member undergoing a brain oxygen-depleting environmental stressor can perform before performance-ending fatigue occurs according to claim 7, wherein the brain oxygen-depleting environmental stressor is high g forces from rapid changes in speed and acceleration of an aircraft and the step of reducing the level of the brain oxygen-depleting environmental stressor is unloading the aircraft.

9. The method for extending the time an aircrew member undergoing a brain oxygen-depleting environmental stressor can perform before performance-ending fatigue occurs according to claim 7, wherein the brain oxygen-depleting environmental stressor is high altitude of an aircraft and the step of reducing the level of the brain oxygen-depleting environmental stressor is reducing the altitude of the aircraft.

* * * * *